United States Patent
Tsuruta et al.

(10) Patent No.: US 7,369,308 B2
(45) Date of Patent: May 6, 2008

(54) TOTAL INTERNAL REFLECTION FLUORESCENCE MICROSCOPE

(75) Inventors: Hiroshi Tsuruta, Machida (JP); Hiroshi Sasaki, Tokyo (JP); Kenichi Kusaka, Hachioji (JP); Akinori Araya, Yokohama (JP); Tatsuo Nakata, Hino (JP)

(73) Assignee: Olympus Corporation, Tokyo (JP)

( * ) Notice: Subject to any disclaimer, the term of this patent is extended or adjusted under 35 U.S.C. 154(b) by 236 days.

(21) Appl. No.: 11/050,883

(22) Filed: Feb. 4, 2005

(65) Prior Publication Data

US 2005/0179903 A1 Aug. 18, 2005

(30) Foreign Application Priority Data

Feb. 9, 2004 (JP) ............................ 2004-032017
Dec. 7, 2004 (JP) ............................ 2004-354621

(51) Int. Cl.
*G02B 21/06* (2006.01)
(52) U.S. Cl. .................... 359/388; 359/385; 250/458.1
(58) Field of Classification Search ..................... None
See application file for complete search history.

(56) References Cited

U.S. PATENT DOCUMENTS

| | | | |
|---|---|---|---|
| 6,255,642 B1 * | 7/2001 | Cragg et al. | 250/216 |
| 6,982,431 B2 * | 1/2006 | Modlin et al. | 250/573 |
| 6,987,609 B2 * | 1/2006 | Tischer et al. | 359/385 |
| 2003/0058530 A1 * | 3/2003 | Kawano | 359/385 |
| 2003/0155527 A1 * | 8/2003 | Natori | 250/458.1 |

FOREIGN PATENT DOCUMENTS

JP 2002-31762 A 1/2002
WO WO 03023483 A2 * 3/2003

OTHER PUBLICATIONS

Daniel Axelrod; "Total Internal Reflection Fluorescence at Biological Surfaces"; Non-Invasive Techniques in Cell Biology; 93-127; 1990 Wiley-Liss, Inc; pp. 111-113.

* cited by examiner

*Primary Examiner*—Stephone B. Allen
*Assistant Examiner*—Derek S. Chapel
(74) *Attorney, Agent, or Firm*—Frishauf, Holtz, Goodman & Chick, P.C.

(57) ABSTRACT

A total internal reflection fluorescence microscope includes a light source which generates laser light having a plurality of wavelengths, a focal optical system which irradiates the laser light from the light source on a specimen at a predetermined incident angle via an objective lens and which generates evanescent illumination, a fluorescence observation unit which observes fluorescence generated from the specimen due to the evanescent illumination, an incident angle adjuster which adjusts the incident angle of the laser light irradiated on the specimen, and a controller which controls the incident angle adjuster such that the amount of the permeation depth of the evanescent light is the same when the wavelength of the laser light from the laser light source is switched.

27 Claims, 4 Drawing Sheets

| Irradiation angle NA | Wavelength | Penetration depth |
| --- | --- | --- |
| 1.4 | 488nm | 165nm |
| | 543nm | 183nm |
| | 633nm | 214nm |

FIG. 4A

| Object magnification | 60 |
| --- | --- |
| Refraction index of cover glass | 1.516 |
| Refraction index of specimen | 1.38 |

FIG. 4B

| Irradiation angle NA | Wavelength | Penetration depth |
| --- | --- | --- |
| 1.4 | 488nm | 165nm |
| 1.40472 | 543nm | |
| 1.41349 | 633nm | |

FIG. 5

TOTAL INTERNAL REFLECTION FLUORESCENCE MICROSCOPE

CROSS-REFERENCE TO RELATED APPLICATIONS

This application is based upon and claims the benefit of priority from prior Japanese Patent Applications No. 2004-032017, filed Feb. 9, 2004; and No. 2004-354621, filed Dec. 7, 2004, the entire contents of both of which are incorporated herein by reference.

BACKGROUND OF THE INVENTION

1. Field of the Invention

The present invention relates to a total internal reflection fluorescence microscope for performing fluorescence observation using evanescent illumination which is generated by total internal reflection illumination.

2. Description of the Background Art

Recently, functional analysis of biological cells has been carried out with enthusiasm. In this type of functional analysis much attention is given to the total internal reflection fluorescence microscope (TIRFM) which obtains total internal reflection images from the cell membrane and surrounding areas, as the microscope for observing cell membrane function.

When the total internal reflection fluorescence microscope totally reflects illumination light at an interface of a cover glass and a specimen, a fluorescent material is excited using light called evanescent light which permeates the limited range of several hundred nm or less at the specimen side. Thus, since only fluorescence in this limited range at the vicinity of the cover glass is observed, the background is extremely dark and high contrast fluorescence observation or weak fluorescence observation are possible.

Meanwhile, at biological research labs which use this type of total internal reflection fluorescence microscope, there are often cases where there is need to observe the in-plane which is not as deep as the interface vicinity with good contrast, as well as cases where the illumination light must reach certain depth and thus wide-range observation needs to be performed. As a result, it is preferable that the permeation depth of the evanescent light is changeable in accordance with the object for observation.

A permeation depth of evanescent light from interfaces is disclosed in Daniel Axelrod "5. Total Internal Reflection Fluorescence at Biological Surfaces", Noninvasive Techniques in Cell Biology: 93-127, 1990, Wiley-Liss, Inc. pp. 111-113, and it is known that the following formula holds true:

$$d=\lambda/4\pi\{(n_1^2\sin\theta_1^2-n_2^2)\}^{1/2} \quad (1)$$

wherein, d is the permeation depth of evanescent light, $\lambda$ is the wavelength of light, $n_1$ is the refractive index at the incidence side (cover glass), $\theta_1$ is the incident angle, and $n_2$ is the refractive index at the exit side (specimen).

Note that the irradiation angle for the specimen NA is obtained as follows.

$$NA=sin\theta_1 \cdot n_1.$$

As is evident from the above formula, the larger the incident angle of the illumination light for the interface of the total reflection irradiation angle, or in other words, the inclination angle of the illumination light for the vertical line of the interface, the deeper the permeation depth for the evanescent light will be.

An example of technology using this type of concept is Jpn. Pat. Appln. KOKAI Publication No. 2002-31762 in which the position of the focal point of the focal light at the rear side focal point in-plane of the objective lens is adjusted by rotation of the reflecting optical system, and the incident angle of the light introduced at the specimen side can be thereby adjusted.

BRIEF SUMMARY OF THE INVENTION

A total internal reflection fluorescence microscope according to a first aspect of the invention comprises: a light source which generates laser light having a plurality of wavelengths; a focal optical system which irradiates the laser light from the light source on a specimen at a predetermined incident angle via an objective lens and which generates evanescent illumination; a fluorescence observation unit which observes fluorescence generated from the specimen due to the evanescent illumination; an incident angle adjuster which adjusts the incident angle of the laser light irradiated on the specimen; and a controller which controls the incident angle adjuster such that the amount of the permeation depth of the evanescent light is the same when the wavelength of the laser light from the laser light source is switched.

A total internal reflection fluorescence microscope according to a second aspect of the invention comprises: a light source which generates laser light having a plurality of wavelengths; a focal optical system which irradiates the laser light from the light source on a specimen at a predetermined incident angle via an objective lens and which generates evanescent illumination; a fluorescence observation unit which observes fluorescence generated from the specimen due to the evanescent illumination; an incident angle adjuster which adjusts the incident angle of the laser light irradiated on the specimen; and a controller which controls the incident angle adjuster such that the permeation depth of the evanescent light is set to a predetermined amount when the wavelength of the laser light from the laser light source is switched.

A total internal reflection fluorescence microscope according to a third aspect of the invention comprises: a light source which generates laser light having a plurality of wavelengths; a varying unit which variably controls the wavelength of the laser light and output intensity; a focal optical system which irradiates the laser light from the light source on a specimen at a predetermined incident angle via an objective lens and which generates evanescent illumination; and a fluorescence observation unit which observes fluorescence generated from the specimen due to the evanescent illumination.

A total internal reflection fluorescence microscope according to a fourth aspect of the invention comprises: a light source; an incident angle controller which controls the incident angle of the illumination light from the light source which is irradiated on the specimen; a permeation depth calculator which calculates the depth of permeation of the specimen for total internal reflection illumination from a control value of the incident angle controller; and a display unit which displays permeation depth calculated by the permeation depth calculator.

A total internal reflection fluorescence microscope according to a fifth aspect of the invention comprises: a light source; an incident angle controller which controls the incident angle of the illumination light from the light source which is irradiated on the specimen; an input unit which inputs a permeation depth of permeation of the specimen for total internal reflection illumination; a condition incident angle calculator which calculates the conditions for calculating the incident angle to set the depth of permeation of the specimen for total internal reflection illumination to the input permeation depth; and a display unit which displays the conditions incident angle obtained by the condition incident angle calculator.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described below with reference to the accompanying drawings.

First Embodiment

Figure 1:
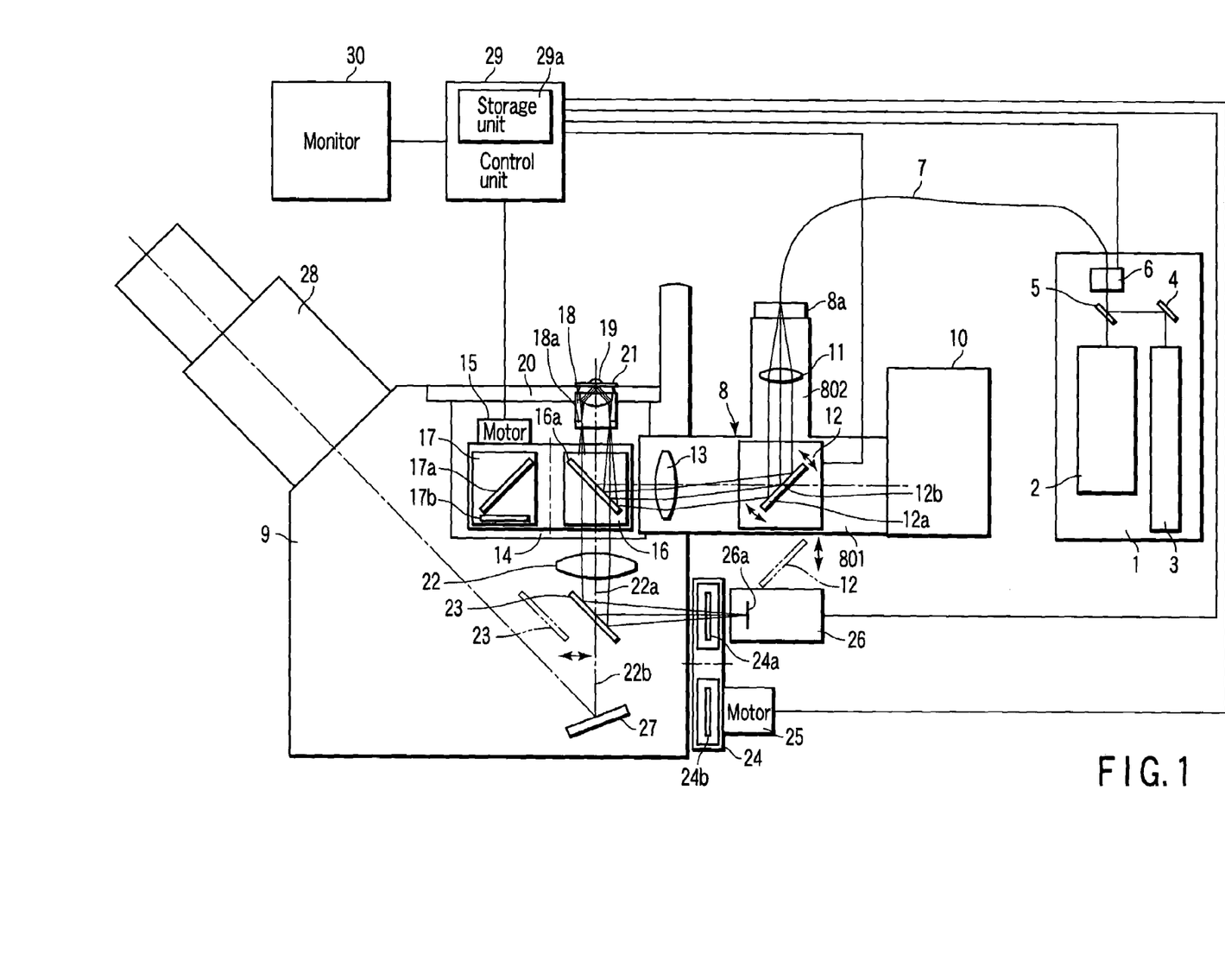
FIG. 1 is a diagram showing a schematic configuration of a first embodiment of the present invention.

FIG. 1 shows a schematic configuration of a total internal reflection fluorescence microscope according to a first embodiment of the invention.

In FIG. 1, a laser unit light source 1 has, for example, an argon (Ar) laser 2 which vibrates 488 nm laser light, and a green helium neon laser 3 which vibrates 543 nm laser light, which are used for evanescent illumination. The laser unit light source 1 may also have a helium neon laser which vibrates 633 nm laser light.

A reflection mirror 4 is disposed on a light path of the laser light from the green helium neon laser 3. A dichroic mirror 5 is disposed on a light path of the laser light from the argon laser 2 at the point of intersection with the laser light reflected at the reflection mirror 4. The dichroic mirror 5 combines the two laser light paths' and transmits the laser light from the argon laser 2 and reflects the laser light reflected at the reflection mirror 4. In other words, the dichroic mirror 5 has a characteristic of reflecting 543 nm laser light and transmitting 488 nm laser light.

An acousto-optic element (AOTF) 6 for wavelength selection is disposed on the light path of the laser light combined by the dichroic mirror 5. In this case, the acousto-optic element 6 selects laser lights having the wavelengths of 488 nm and 543 nm and is capable of switching each of the wavelengths. Note that an electro-optic element or a liquid crystal shutter may be used in place of the acousto-optic element.

Note that another example of wavelength selection means is a method in which a plurality of laser diode (LD) light sources which generate laser lights of different wavelengths are aligned and a value of current to be supplied to a power source of the LD light sources is varied and turned on and off, whereby a laser light of a desired wavelength is selected.

An exit end of the acousto-optic element 6 has an incidence end of the fiber 7 disposed thereon and leads the laser light for evanescent illumination to an evanescent projecting tube 8 serving as a vertical light projecting tube via the fiber 7.

The evanescent projecting tube 8 comprises a linear projecting tube body 801 and a light guiding tube 802 which projects in the direction orthogonal the projecting tube body 801. One end of the projecting tube body 801 is fixed by screws (not shown) to a vertical light projecting tube attachment portion of a standing microscope body 9.

The evanescent projecting tube 8 has a light source 10 for vertical illumination provided at the other end of the projecting tube body 801. As the light source 10 for vertical illumination, for example, a mercury lamp may be used for the purpose of the vertical fluorescence illumination for a normal microscope.

A laser introducing section 8a is provided at the front end of the light guiding tube 802 of the evanescent projecting tube 8. An exit end of the fiber 7 is connected to the laser introduction section 8a.

A collimate lens 11 and a galvano mirror unit 12 serving as incident angle adjusting means are disposed on the light path of the laser light which exits from the end of the fiber 7. The collimate lens 11 converts divergent light emitted from the fiber 7 to parallel light. The galvano mirror unit 12 has a galvano mirror 12a as a deflection mirror disposed at the point of intersection of a light path for the illumination light of the vertical illumination light source 10 and a light path for the laser light from the end of the fiber 7. The galvano mirror 12a is rotated about a rotation axle 12b by an electrically driven mechanism (not shown) and thus deflection of the laser light (excitation light) from the fiber 7 is possible. Also, the galvano mirror unit 12 is insertable in and removable from the light path by using a switching mechanism (not shown). That is, by insertion in/removal from the light path, the galvano mirror unit 12 switches the light path of the evanescent illumination from the fiber 7 and normal vertical fluorescence illumination from the vertical illumination light source 10. In the example shown in the drawing, in a state in which the galvano mirror unit 12 is inserted in the light path, the switch has been made to the state for performing evanescent illumination.

A condensing lens 13 which constitutes a condensing optical system is disposed on a reflected light path of the galvano mirror 12a. The condensing lens 13 condenses light at a surface of the exit end of the fiber 7 on a pupil position 18a which is a rear side focal position of an objective lens 18 described later.

The light path of the laser light which exits from the condensing lens 13 has a cube turret 14 disposed thereon. The cube turret 14 can hold a plurality of cube units, and is configured such that rotational switching is made possible by a monitor 15 via a sliding mechanism such a bearing mechanism (not shown). In the example shown in the drawing, two types of cube units 16 and 17 are installed, and the cube unit 16 is positioned in the light path for the laser light from the condensing lens 13.

The cube unit 16 has an excitation dichroic mirror 16a as a wavelength selection optical element. The excitation dichroic mirror 16a has characteristics of reflecting lights having wavelengths of 488 nm and 543 nm as excitation light, and transmitting fluorescent lights having wavelengths of 500 to 540 nm and 560 nm generated by a specimen 19 due to the excitation light. In addition, the cube unit 17 has a dichroic mirror 17a and a barrier filter 17b as a wavelength selection optical element. The dichroic mirror 17a has characteristics of reflecting light of a predetermined wavelength from the light source 10 for vertical illumination and transmitting fluorescent light generated from the specimen 19 due to the light. The barrier filter 17b transmits only light having the necessary fluorescent wavelength from the fluorescence generated from the specimen 19. In the case where there is other fluorescence to be observed, the cube units 16 and 17 may be removed from the cube turret 14 and replaced by another cube unit.

The reflected light path of the excitation dichroic mirror 16a of the cube unit 16 (which is positioned on the light path for the laser light from the condensing lens 13) has the objective lens 18 disposed thereon.

The specimen 19 which has been dyed with a fluorescent dye is disposed at the front side focus position of the objective lens 18. The specimen 19 is disposed on a stage 20 of the standing microscope body 9 and a cover glass 21 is fixed thereto. In this case, high NA is ensured at the area between the cover glass 21 and the objective lens 18 is filled with emulsion oil for causing total internal reflection due to the evanescent illumination.

A focusing lens 22 and a reflection mirror 23 which constitute an observation optical system are disposed on a transmitted light path 22a of the excitation dichroic mirror 16a of the cube unit 16 (which is positioned in the light path for the laser light from the condensing lens 13).

The reflection mirror 23 can be inserted in and removed from the light path by the switching mechanism (not shown). In this case, the insertion in/removal from the light path of the reflection mirror may be performed independently or may be performed along with the insertion in/removal from the light path of the galvano mirror unit 12. The example shown in the drawings shows a state in which the reflection mirror 23 has been inserted in the light path.

In the state in which the reflection mirror 23 has been inserted in the light path, a filter wheel 24 which constitutes fluorescence observation unit is disposed on the reflected light path of the reflection mirror 23. The filter wheel 24 holds a plurality (two in the example shown in the drawing) of filters 24a and 24b and can be switched onto the light path by the monitor 25 via the sliding mechanism (not shown). In this case, the filter 24a transmits fluorescence generated by an excitation wavelength of 488 nm, and the filter 24b transmits fluorescence generated by an excitation wavelength of 543 nm, for example. Note that, in the example shown in the drawing, the filter 24a is positioned on the light path.

A CCD camera 26 serving as image pickup means is disposed on the light path transmitted by the filter wheel 24. At the CCD camera 26, fluorescence from the specimen 19 transmitted by the focusing lens 22 is led to and focused on an image pickup plane 26a.

When the reflection mirror 23 is removed from the light path, a reflection mirror 27 and a visual observation unit 28 are disposed on a visual observation path 22b. At the visual observation unit 28, the fluorescence that is selected from the fluorescence from the specimen 19 by the barrier filter 17b which is provided at the cube unit 17 is transmitted by the focusing lens 22, and visual observation is thereby performed.

Meanwhile, a control unit 29 serving as control means is connected to the acousto-optic element 6, the motor 15 which drives the cube turret 14 by rotation, the motor which drives the filter wheel 24 by rotation, and the CCD camera 6. The control unit 29 outputs a control signal to the acousto-optic element 6, the motors 15 and 25 and the CCD camera 26, and also processes image data picked up by the CCD camera 26 and displays it at a monitor 30. In addition, the control unit 29 has a storage unit 29a as storage means.

In this case, the control unit 29 obtains the incident angle $\theta_1$ for making the permeation depth d of the evanescent light the same for each of the excitation wavelengths of the argon laser 2 and the green helium neon laser 3 of the laser source unit 1 by calculation. The angle of the galvano mirror 12 for obtaining the incident angle $\theta_1$ is stored in the storage unit 29a as control information. In the case where fluorescence observation is performed with the permeation depth d of the evanescent light being the same amount, the corresponding control information is read from the storage unit 29a in accordance with the switching of the laser wavelengths by the argon laser 2 and the green helium neon laser 3, and the angle of the galvano mirror 12a is thereby controlled.

Further, the control unit 29 determines the angles of incidence $\theta_1$ for obtaining the permeation depth d of different evanescent lights for each of the laser wavelengths of the argon laser 2 and the green helium neon laser 3 of the laser source unit 1. Angle information of the galvano mirror 12a for obtaining these angles of incidence $\theta_1$ is stored in the storage unit 29a. Also, in the case when fluorescence observation is performed while changing the permeation depth d of the evanescent light, if the permeation depth d of the evanescent light is specified, the angle information corresponding to the argon laser 2 or the green helium neon laser is read from the storage unit 29a, and the angle of the galvano mirror 12a is thereby controlled.

The functions of the embodiment having the above configuration will be described in the following.

First, there is described a case where the cube unit 16 is switched on the light path by the control unit 29, and the laser lights from argon laser 2 which vibrates laser light with a wavelength of 488 nm and the green helium neon laser 3 which vibrates laser light with a wavelength of 543 nm in the laser source unit 1 are respectively used to irradiate the specimen 19, whereby the fluorescence generated from the specimen 19 is obtained. In this case, the specimen 19 is one which is dyed twice with fluorescent dyes having fluorescent wavelength peaks of 520 nm and 580 nm, respectively.

In this state, the control unit 29 generates a trigger signal which shows the start timing for image acquisition and the end timing for image acquisition (or the image acquisition timing and the image acquisition time) for the CCD camera 26; an instruction signal for selecting the laser light with a wavelength of 488 nm which is vibrated from the argon laser 2 of the laser source unit 1 for the acousto-optic element 6; and a trigger signal which shows the start timing for irradiation and the end timing for irradiation (or the start timing for irradiation and irradiation time). While the acousto-optic element 6 is driven and the laser is irradiated, the CCD camera 26 is driven so as to perform exposure.

Furthermore, when the excitation wavelength is switched and visual observation is performed due to total internal reflection irradiation, if the excitation wavelength changes, the permeation depth of the evanescent light changes. The angle of the galvano mirror 12a is sometimes switched for each excitation wavelength in order to correct the change. In this case, the control unit 29 generates a signal for driving the galvano mirror 12a as well, in synchrony with the instruction signal for the CD camera 26 and the acousto-optic element 6. While the acousto-optic element 6 is driven and laser is output, the galvano mirror 12a is driven so as to be fixed at a predetermined angle.

Subsequently, instruction is sent to the monitor 15, and the cube turret 14 is driven such that the cube unit 16 is positioned on the light path. Furthermore, instruction is also sent to the monitor 25, and the filter wheel 24 is rotated to insert the filter 24a in the light path.

In this state, the laser wavelength of 488 nm which is vibrated from the argon laser 2 is transmitted by the dichroic mirror 5 and the acousto-optic element 6, and led to the incident end of the fiber 7.

The laser light which is emitted from the fiber 7 is reflected at the galvano mirror 12a of the galvano mirror unit 12 via the collimate lens 11 of the evanescent projecting tube 8. In this case, if the permeation depth d of the evanescent light is specified in advance, the angle information (corresponding to the argon laser 2) of the galvano mirror 12a for obtaining the permeation depth d is read from the storage unit 29a, and the angle of the galvano mirror 12a is thereby controlled.

The light reflected by the galvano mirror 12a passes through the condensing lens 13 and is led to the cube unit 16. Since the excitation dichroic mirror 16a which is loaded in the cube unit 16 reflects 488 nm wavelength, the laser light is reflected upward and is condensed at the end of the pupil position 18a of the rear side focal point position of the objective lens 18. The laser light which is condensed at the pupil position 18a of the objective lens 18 irradiates the specimen side interface of the cover glass 21 from a slant direction at a predetermined angle. This angle is set to be the angle for which the laser light causes total internal reflection, and as a result, only a portion of the laser light permeates from the specimen side interface of the cover glass 21 to the specimen 19 side, so that the light which permeates in the depth direction of the specimen 19 is generated as evanescent light.

If the specimen 19 emits fluorescence due to illumination of this type of evanescent light, the fluorescence (500 to 540 nm) is transmitted by the objective lens 18, and is then transmitted by the excitation dichroic mirror 16a in the cube unit 16 to be incident to the focusing lens 22. In addition, the fluorescence is reflected by the reflection mirror 23 and then imaged on the image pickup plane 26a of the CCD camera 26 via the filter 24a of the filter wheel 24, and the image is picked up as a fluorescence observation image by evanescent illumination. The picked-up image data is stored in the storage unit 29a of the control unit 29 as a fluorescence (500 to 540 nm) image when the specimen 19 is irradiated with a laser of wavelength 488 nm which is vibrated from the argon laser 2.

Next, the control unit 29 generates a trigger signal which shows the start timing for image acquisition and the end timing for image acquisition (or the image acquisition timing and the image acquisition time) for the CCD camera 26; an instruction signal for selecting the laser light with a wavelength of 543 nm which is vibrated from the green helium neon laser 3 of the laser source unit 1 for the acousto-optic element 6; and a trigger signal which shows the start timing for irradiation and the end timing for irradiation (or the start timing for irradiation and irradiation time). While the acousto-optic element 6 is driven and the laser is irradiated, the CCD camera is driven so as to perform exposure.

The image is then picked up for fluorescence observation by the evanescent light at the CCD camera 26 in the same manner as in the case where excitation is performed by the 488 nm laser.

The picked-up image data is stored in the storage unit 29a of the control unit 29 as a fluorescence (580 nm) image when the specimen 19 is irradiated with laser wavelength of 543 nm which is vibrated from the argon laser 2.

In this state, the light which is reflected at the galvano mirror 12a passes through the condensing lens 13, is led to the cube unit 16, and is then reflected by the excitation dichroic mirror 16a. The light condensed at the end of the pupil position 18a of the rear side focal position of the objective lens 18, and evanescent light which permeates in the depth direction of the specimen 19 is generated as described above.

In this case, because the angle is also controlled based on the control information stored in the storage unit 29a in order to make the permeation depth of the evanescent light the same amount due to the switching of the argon laser 2 and the green helium neon laser 3, the permeation depth d of the evanescent light which permeates in the depth direction of the specimen 19 is kept fixed regardless of the switching of the wavelength of the laser light.

When fluorescence is emitted from the specimen 19 by the illumination of the evanescent light, the fluorescence is transmitted by the objective lens 18, and then transmitted by the excitation dichroic mirror 16a in the cube unit 16. The fluorescence is reflected by the reflection mirror 23 via the focusing lens 22 and then focused on the image pickup plane 26a of the CCD camera 26 via the filter 24b, and the image is picked up as a fluorescence observation image due to evanescent illumination.

Accordingly, for the specimen 19 which has been dyed a number of times by a plurality of fluorescent dyes, even in the case where the argon laser 2 and the green helium neon laser 3 which have different wavelengths are to be switched, because the angle of the galvano mirror 12a is controlled based on the control information stored in advance in the storage unit 29a in accordance with the switching of the argon laser 2 and the green helium neon laser 3, the permeation depth d of the evanescent light can always be set to the same amount by switching the wavelengths of these laser lights as well. That is, because the permeation depth d of the evanescent light can always be the same amount regardless of the excitation wavelength from the laser light, the troublesome operation of adjusting of the incident angle for each excitation wavelength which has been required by the microscopes of the prior art can be omitted, so that the desired fluorescence observation can be easily realized.

Of course, in the case where the observation is to be performed while changing the permeation depth d of the evanescent light using the argon laser 2 and the green helium neon laser 3, respectively, if the desired permeation depth d of the evanescent light is specified, the angle of the galvano mirror 12a is controlled by the angle information stored in advance in the storage unit 29a and can be easily caused to match the respective observations.

In addition, because following the switching of the laser wavelengths by the argon laser 2 and the green helium neon laser 3, the filter wheel 24 is driven and the optimum filters 24a and 24b for the selected excitation wavelength are automatically inserted in the light path, the optimum fluorescence images for the excitation wavelengths can be obtained with certainty. In this case, because of the switching of the excitation wavelengths, these fluorescence images can be quickly obtained. Therefore, the respective fluorescence images can be instantaneously switched and displayed on the monitor, and multiple fluorescence images can be displayed at the same time.

The description so far has been that in which the filter is switched and excitation wavelengths of 488 nm and 543 nm respectively are obtained. However, if the filter 24a is made to transmit fluorescence generated when excitation is performed by both 488 nm and 543 nm, the filter does not need to be changed, and by simply switching the excitation wavelength, the fluorescence excitation by the respective excitation wavelengths can be identified as different fluorescence wavelengths from the specimens which have been subjected to multiple dying. As a result, the effect of speedily and selectively obtaining fluorescence from specimens which have been subjected to multiple dying can be obtained.

Laser lights with a plurality of wavelengths are stably controlled, and synchronized with a detecting system, whereby fluorescence can be speedily and selectively obtained from specimens which have been subjected to multiple dying, so that each fluorescence image can be switched and displayed on the monitor 30, and a plurality of fluorescence images can be displayed at the same time.

Modified Example of First Embodiment

Figure 2:
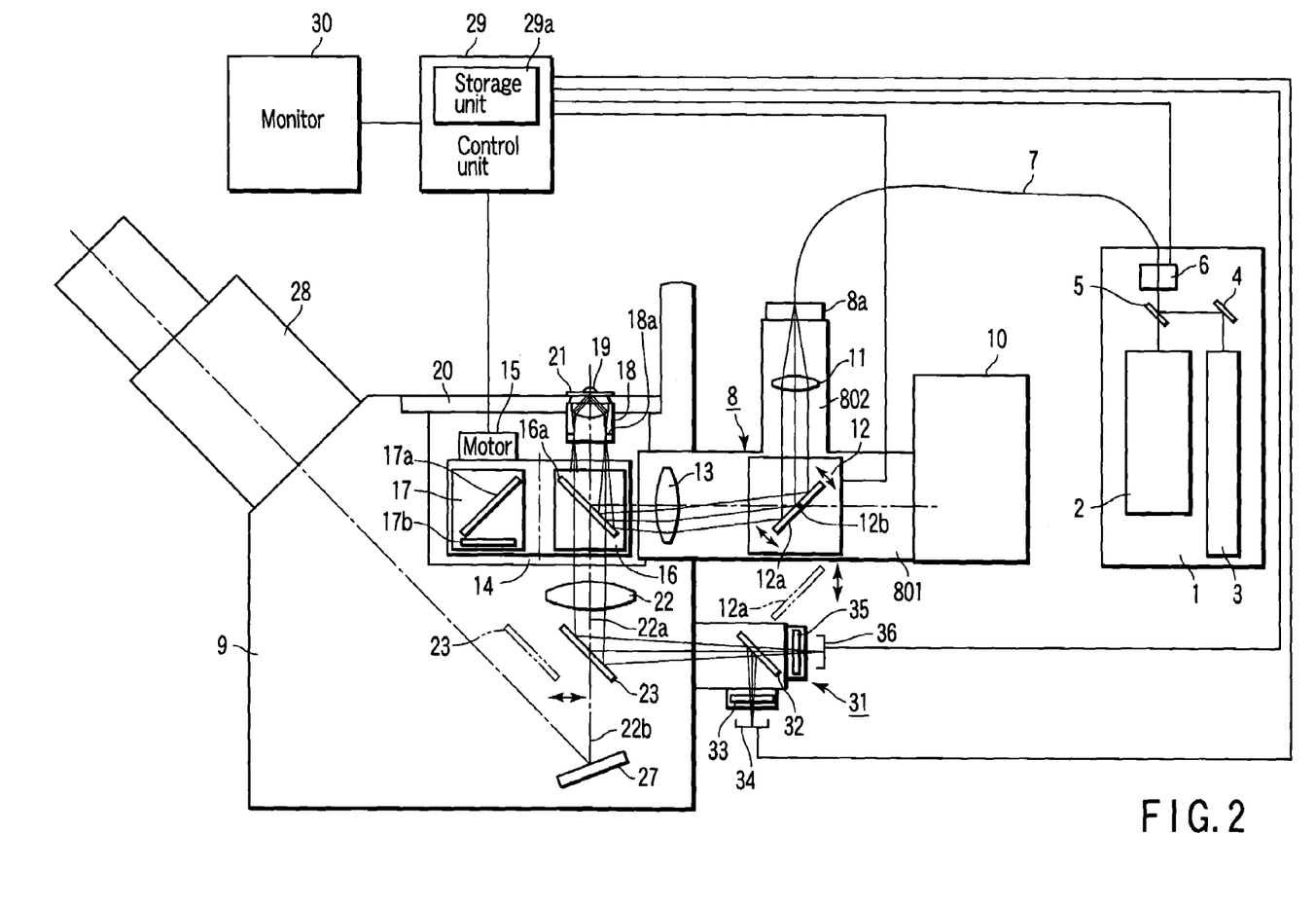
FIG. 2 is a diagram showing a schematic configuration of a modified example of the first embodiment.

FIG. 2 is a diagram showing a schematic configuration of a modified example of the first embodiment of the invention and those portions which are the same as the first embodiment have been assigned the same numbers.

In this case, the filter wheel 24 which is disposed on the reflected light path of the reflection mirror 23 is replaced by a fluorescence detecting unit 31. At the reflection detecting unit 31, a spectroscopic dichroic mirror 32 is disposed on the reflected light path of the reflection mirror 23. The spectroscopic dichroic mirror 32 has characteristics of reflecting the long wavelength fluorescence and transmitting short wavelength fluorescence. The reflection side light path of the spectroscopic dichroic mirror 32 has a barrier filter 33 and a detector 34, and the transmission side light path has a barrier filter 35 and a detector 36. The barrier filters 33 and 35 filter only the fluorescence wavelength region for which detection is desired.

The detectors 34 and 36 convert the detected fluorescence to electrical signals and outputs the signals to the control unit 29. The control unit 29 creates fluorescence images using the signals from the detectors 34 and 36, and the fluorescence images are displayed on the monitor 30.

Aside from this, everything is the same as in FIG. 1.

With this type of configuration, the output from the detectors 34 and 36 can be selectively retrieved from the control unit 29 in accordance with the switching of the laser wavelength using the argon laser 2 and the green helium neon laser 3. Therefore, the above-mentioned filter wheel 24 is mechanically driven, and many types of fluorescence images can be obtained more quickly than in the case where the filters 24a and 24b are inserted in the light path, so that fluorescence observation can be performed efficiently.

Furthermore, in addition to the effects of the first embodiment, the fluorescence which is excited by the argon laser 2 and the fluorescence which is excited by the green helium neon laser 3 can be observed simultaneously without switching the wavelengths of the lasers using the argon laser 2 and the green helium neon laser 3.

Second Embodiment

A second embodiment of the present invention will be described in the following.

Figure 3:
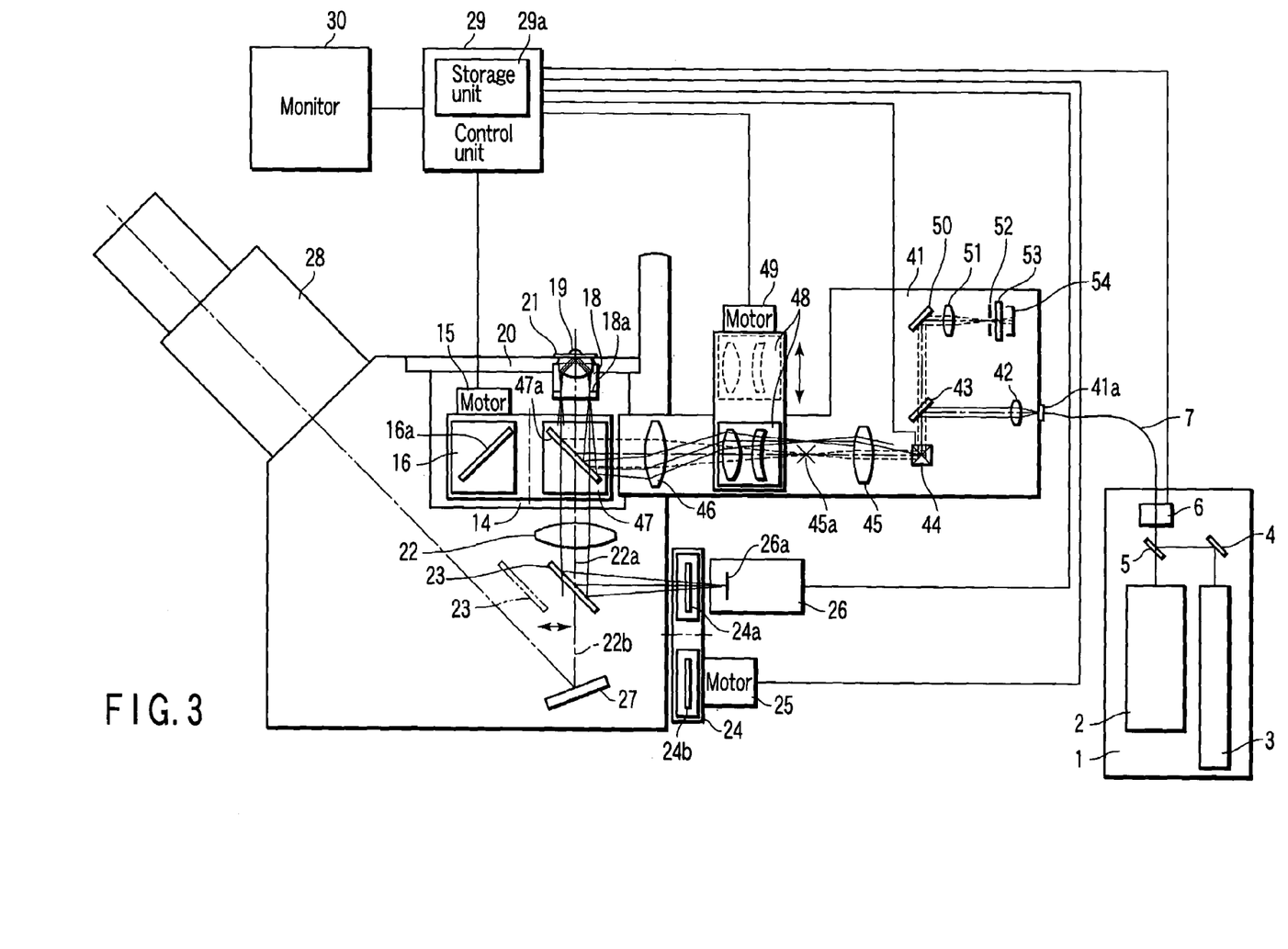
FIG. 3 is a diagram showing a schematic configuration of a second embodiment of the present invention.

The second embodiment comprises a scanning unit in which laser light is deflected by a light scanning mirror for the total internal reflection fluorescence microscope which performs evanescent illumination, and the spotlight on the specimen does two-dimensional scanning, and the fluorescence generated from the specimen is subjected to confocal observation via a confocal pinhole.

FIG. 3 shows a schematic configuration of the second embodiment of the invention, and those portions which are the same as the first embodiment have been assigned the same numbers.

In this case, the laser source unit 1 is used in common for evanescent illumination and confocal observation, and the evanescent projecting tube is replaced with a scanning unit 41.

In addition, the exit end of the acousto-optic element 6 of the laser source unit 1 is connected to the scanning unit 41 via the fiber 7.

The scanning unit 41 has a laser light introduction port 41a which introduces laser light irradiated from the fiber 7. Further, a collimate lens 42 and an excitation dichroic mirror 43 are disposed on the light path of the outgoing laser light from the laser light introduction port 41a.

The collimate lens 42 converts the outgoing laser light from the laser light introduction port 41a into collimate light. The excitation dichroic mirror 43 has characteristics of reflecting the laser light wavelength (488 nm and 543 nm) and transmitting the wavelength region of the fluorescence which is emitted from the specimen 19.

A light deflection mirror unit 44 serving as light scanning means is disposed on the reflected light path of the excitation dichroic mirror 43. The light deflection mirror unit 44 has two sets of galvano scanner mirrors which deflect light in the vertical direction with respect to the paper surface and in the direction perpendicular to the paper surface, and the laser light is scanned in the two-dimensional direction by these galvano scanner mirrors.

The light path for the laser light irradiated by the light deflection mirror unit 44 has an aperture projection lens 45 disposed thereon. A condensing lens 46 is disposed on the light path of the outgoing laser light from the aperture projection lens 45. The condensing lens 46 converts the outgoing laser light from the aperture projection lens 45 to parallel light (the light path shown by the dotted line) and it is made incident on a cube turret 47 to which a reflection mirror 47a is mounted and which is installed on the cube turret 14.

Reference numeral 48 is a lens unit for evanescent illumination, which is inserted in the light path only at the time of evanescent illumination, and is removed from the light path for confocal observation. In other words, for evanescent illumination, the laser light must be condensed on the pupil position 18a of the objective lens 18. Thus, in order to cause a focal position 45a on which light is condensed by the aperture projection lens 45 to be focused at the pupil position 18a of the objective lens 18, the lens unit 48 can be inserted in the light path. In addition, the lens unit 48 is moved in the direction of the arrow in the drawing by a motor 49 which is driven by instruction from the control unit 29, thereby enabling insertion in/removal from the light path.

On the other hand, a reflection mirror 50 which constitutes confocal observation means, a confocal lens 51, a confocal pin hole 52, a barrier filter 53 which cuts out the excitation laser light and takes the fluorescent wavelength region which is to be detected, and a photodetector 54 are disposed on the transmission light path of the excitation dichroic mirror 43. For example, a photomultiplier may be used as the photodetector herein.

First, confocal observation will be described for this type of configuration.

In the case of this type of configuration, laser light from the laser source unit 1 is emitted by the acousto-optic element 6, and is introduced into the laser light introduction port 41*a* of the scanner unit 41 via the fiber 7. The laser light is converted to parallel light by the collimate lens 42, is reflected downward as the excited laser light by the excitation dichroic mirror 43, and is made incident on the light deflection mirror unit 44.

The light deflection mirror unit 44 deflects the laser lights using two sets of galvano scanner mirrors which deflect the light in the vertical direction with respect to the paper surface and in the perpendicular direction with respect to the paper surface. Then, the laser light which is deflected at the light deflection mirror unit 44 is transmitted by the aperture projection lens 45 and is converted to parallel light by the condensing lens 46 (the light path shown by the dotted line). At this time, the lens unit 48 for evanescent illumination is removed from the light path.

The laser light which is converted to parallel light at the condensing lens 46 is reflected upward by the reflection mirror 47*a* of the cube unit 47, the parallel light is made incident on the objective lens 18, and the light is condensed by the objective lens 18 and connects with the light spot of the specimen 19. This light spot is two-dimensionally scanned on the specimen 19 by the light deflection of the light deflection mirror unit 44.

If fluorescence is emitted due to two-dimensional scanning of the light spot on the specimen 19, the fluorescence proceeds in the opposite direction to the excitation laser light and reaches the excitation dichroic mirror 43 via the condensing lens 46, the aperture projection lens 45, and the light deflection mirror unit 44. The fluorescence having reached the excitation dichroic mirror 43 is transmitted by the excitation dichroic mirror 43 and reflected by the reflection mirror 50. The fluorescence then passes through the confocal lens 51, the confocal pinhole 52, and the barrier filter 53 and is detected by the photodetector 54.

Fluorescence observation by evanescent illumination will be described next.

In the confocal observation described above, the laser light must be made incident on the objective lens 18 as a parallel beam. On the contrary, in evanescent illumination, the laser light must be condensed on the pupil position 18*a* of the objective lens 18. As a result, the lens unit 48 for focusing the focal position 45*a* where light is condensed using the aperture projection lens 45 at the pupil position 18*a* of the objective lens 18 is inserted in the light path.

In addition, in order to control the position for image focusing on the pupil position 18*a* of the objective lens 18, one galvano scanner mirror (which deflects in the vertical direction with respect to the paper surface) of the light deflection mirror unit 44 including two sets of galvano mirrors is used, the galvano scanner mirror causes deflection, the focal position 45*a* is changed by the aperture projection lens 45, and the condensing position is changed at the pupil position 18*a* of the objective lens 18 which is optically conjugated with image focusing position 45, whereby control is performed.

In this case also, the control unit 29 determines the angles of incidence $\theta_1$ for making the permeation depth d of the evanescent light the same for each of the laser wavelengths of the argon laser 2 and the green helium neon laser 3 of the laser source unit 1 by calculation. The angle of one galvano scanner mirror in the light deflection mirror unit 44 for obtaining the angles of incidence $\theta_1$ is stored in the storage unit 29*a* as control information. In the case where fluorescence observation is performed with the permeation depth d of the evanescent light fixed, the corresponding control information is read from the storage unit 29*a* in accordance with the switching of the excitation wavelengths by the argon laser 2 and the green helium neon laser 3, the angle of one galvano scanner mirror in the light deflection mirror unit 44 is thereby controlled, the focal position 45*a* is changed using the aperture projection lens 45, and the condensing position at the pupil position 18*a* of the objective lens 18 which is optically conjugated with the focal position 45*a* is changed.

The control unit 29 rotates the cube turret 14 by fluorescence observation due to evanescent illumination, and the cube unit 16 having the excitation dichroic mirror 16*a* installed therein is inserted in the light path.

Due to this state, the laser light for evanescent illumination from the laser source unit 1 is lead from the aperture projection lens 45 to the excitation dichroic mirror 16*a* of the cube unit 16 via the lens unit 48 and the condensing lens 46. The laser light is then reflected at the objective lens 18 and condensed at the pupil position 18*a* of the objective lens 18, and the specimen 19 is subjected evanescent illumination via the objective lens 18.

In this case, even if switching of the argon laser 2 and the green helium neon laser 3 is performed, because the angle for one galvano scanner mirror in the deflection mirror unit 44 is controlled based on the control information stored in the storage unit 29*a* for making the permeation depth d of the evanescent light the same amount, the permeation depth d of the evanescent light which permeates the depth direction of the specimen 19 is kept fixed regardless of the switching of the wavelength of the laser light.

The fluorescence emitted from the specimen 19 due to evanescent illumination is picked up by the CCD camera 26 in the same manner as in the above-described first embodiment.

By having this configuration, the argon laser 2 and the green helium neon laser 3 having different wavelengths are switched for the specimen 19 which has been subjected to various types of dying with multiple dyes. Even in such a case, because the angle of one galvano scanner mirror in the light deflection mirror unit 44 is controlled based on the control information stored in advance in the storage unit 29*a* in accordance with the switching of the argon laser 2 and the green helium neon laser 3, the permeation depth d of the evanescent light can always be kept constant by switching the wavelengths of these laser lights, and the same effects as the first embodiment are obtained.

Of course, in the case where the observation is to be performed while changing the permeation depth d of each of the evanescent lights by using the argon laser 2 and the green helium neon laser 3, if the desired permeation depth d of the evanescent light is specified, the angle of one galvano scanner mirror in the light deflection mirror unit 44 is controlled by the angle information stored in advance in the storage unit 29*a*, and can be easily caused to correspond with the respective observations.

Furthermore, the laser source unit 1 may be used in common. The control unit 29 controls the insertion/removal of the lens unit 48 in/from the light path, whereby total internal reflection fluorescence observation and scan fluorescence observation of a multiple dyed fluorescence specimen can be easily performed.

In the above-described first and second embodiments, in the case where the CCD 26 and the detectors 34 and 36 do not receive control signals from the control unit 29 (for example, in the case where the detector is a stand alone device), the CCD 26 and the detectors 34 and 36 can give synchronized signals for the starting image retrieval and the image data to the control unit 29.

In this case, when the synchronized signal for starting image retrieval is sent to the control unit 29 from the CCD camera 26, in synchronization therewith, the control unit 29 outputs instruction signals for selecting the 488 nm wavelength which is vibrated from the argon laser 2 of the laser source unit 1 and timing signals for starting irradiation to the acousto-optic element 6. While the CCD camera 26 is performing exposure, the acousto-optic element 6 is driven so as to output the laser. The galvano scanner mirror is also driven by signals from the CCD camera 26.

Following this, imaging is performed in the form of fluorescence observation by evanescent illumination with the CCD camera 26 and the detectors 34 and 36 in the same manner as in the first and second embodiments.

Accordingly, the effects of the first and second embodiments may be obtained by adding detector units such as commercially available CCDs at a later time. In other words, the user may modify the device and thus the degree of freedom for experimentation is wider.

In the above-described embodiments, the permeation depth of the evanescent light may be freely adjusted, and the wavelength of the laser light and the output intensity may be variably controlled. When the permeation depth is calculated from the irradiation angle, and the calculation result is displayed, the display is convenient when adjusting the permeation depth. This embodiment will be described with reference to FIGS. 4 to 7. The configuration of this embodiment is the same as that of FIGS. 1 to 3 and thus the drawings and detailed descriptions thereof will be omitted.

Third Embodiment

A third embodiment of the present invention will be described with reference to FIG. 4. FIG. 4 shows a display example of the monitor 30 in FIG. 1 according to the third embodiment.

Figure 4A:
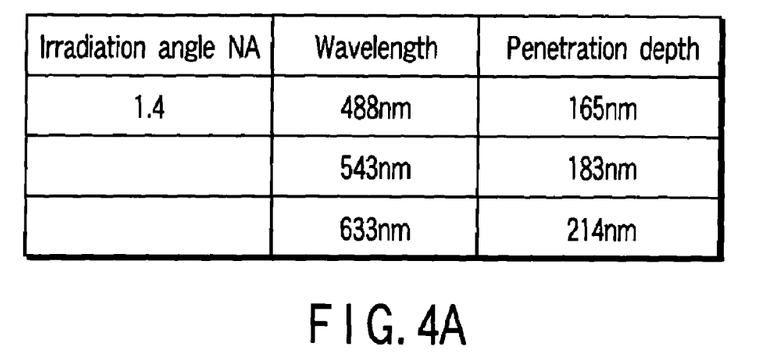
FIGS. 4A and 4B show a display example according to the third embodiment.
Figure 4B:
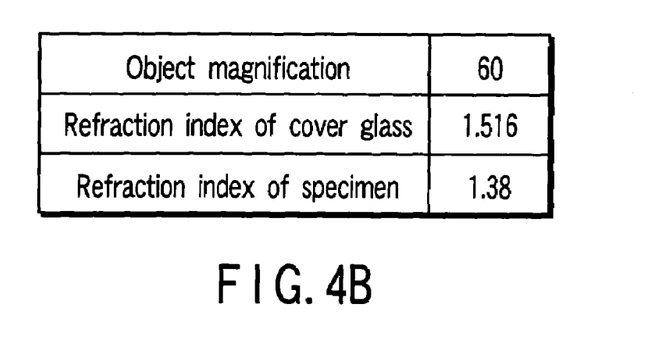

An observer adjusts (specifies) the angle (referred to as galvano angle hereinafter) of the galvano mirror 12*a* of the galvano mirror unit 12 using input means (not shown), while checking an image of a specimen having a wavelength of 480 nm with the CCD camera 26. At this time, the irradiation angle NA of the specimen from the galvano angle which has been specified is determined using the optical properties of the condensing lens 13 and the objective lens 18 shown in FIG. 1 (values in italics in FIG. 4A). The permeation depth for each wavelength is calculated from the irradiation angle NA using Formula (1), and the results are displayed as shown in FIG. 4A, for example. The example of FIG. 4A shows a list of the results of the calculations where when the irradiation angle NA is 1.4, the permeation depths for the wavelengths 488 nm, 543 nm, and 633 nm are 165 nm, 183 nm, and 214 nm, respectively. The magnification of the objectives, the refractive index of the cover glass and the refractive index of the specimen are displayed as shown in FIG. 4B (in the other modified examples, FIG. 4B is the same and thus it will be omitted in the description thereof). Note that when the objectives is switched, a sensor (not shown) detects the magnification of the objectives that is disposed on the light path at that time, and the results of the detection are displayed. Also, the refractive indices of the cover glass and specimen can be selected based on the materials thereof, whereby the refractive indices stored in the storage unit 29*a* can be displayed. Values for the magnification of the objectives, the refractive index of the cover glass and the refractive index of the specimen which are shown in FIG. 4B may be input by the observer. According to this embodiment, the conditions for obtaining the objective permeation depth can be determined, and thus, the user can easily recognize the current permeation depth, for example, when adjusting the irradiation angle while observing the specimen. Furthermore, the permeation depth for all the wavelengths can be easily recognized.

First Modified Example of Third Embodiment

Figure 5:
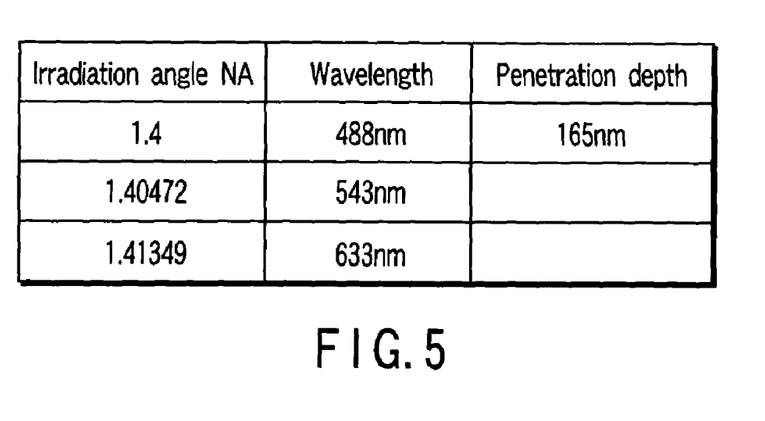
FIG. 5 shows display examples according to first and second modified examples of the third embodiment.

FIG. 5 shows an example of the display according to a first modified example of the third embodiment. In this modified example, the irradiation angle NA is displayed such that when the irradiation angle is set to one wavelength, the permeation depth is the same for other angles.

The galvano angle is specified using input means (not shown) while checking an image for a specimen having a wavelength of 488 nm using the visual observation unit 28. Next, the irradiation angle NA of the specimen is calculated from the specified galvano angle (in this case NA=1.4). The permeation depth for the wavelength of 488 nm is then calculated from the irradiation angle NA obtained, and the results are then displayed (permeation depth=165 nm). In the case where the permeation depth of 165 nm is to be maintained when the wavelength is 488 nm, the irradiation angle NA for each wavelength is calculated and displayed. In this case, when the wavelength is 488 nm and NA=1.4, the permeation depth is 165 nm and the irradiation angle NA is 1.40472 and 1.41349 for wavelengths of 543 nm and 633 nm, respectively.

In this modified example, if the irradiation angle is set at one wavelength for observing a multiple dyed specimen, wavelength for all angles of irradiation which cause the same permeation depth can be determined, and the irradiation angle can be easily set such that the permeation depth of each of the wavelengths is constant.

Second Modified Example of Third Embodiment

An example of the display according to a second modified example of the third embodiment is the same as in FIG. 5, and thus the drawing thereof is omitted. In this modified example, the irradiation angle NA for the case where the permeation depth is set is displayed. The difference between this and the first modified example is described in the following. In the first modified example, the galvano angle is adjusted while viewing the image having a wavelength of 488 nm, the irradiation angle NA is calculated from the galvano angle, and then the permeation depth is calculated from the irradiation angle NA. However, in this modified example, the user inputs the permeation depth, and the irradiation angle NA for all the wavelengths is calculated for the permeation depth and then displayed.

In this modified example, as described above, when a predetermined permeation depth is set, the conditions for realizing this permeation depth can be determined. Furthermore, when observing a multiple dyed specimen, if the irradiation angle is set at one wavelength, all the wavelengths for the irradiation angle which allow the same permeation depth can be determined, and the irradiation angle for causing the permeation depth to be constant for each wavelength can be easily set.

Note that this invention is not limited to the configurations described above, and various modifications may be made without departing from the scope of the invention when it is put into practical use. For example, in the first embodiment described above, the galvano mirror unit 12 is used as the incident angle adjusting means, but the galvano mirror unit 12 may be replaced by a reflection mirror, and the exit end of the laser light to the evanescent projecting tube 8 may be made moveable in the horizontal direction by the fiber 7, so that the incident angle of the laser light for illuminating the specimen may also be adjusted by changing the irradiation position of the laser light from the reflection mirror. Furthermore, each of the embodiments has been described separately, but they may be suitably used in combination. For example, combinations of the first embodiment and the third embodiment, and the second embodiment and third embodiment and the various other combinations may be used. Also the above-described embodiments include inventions at various stages and various inventions can be extracted by suitably combining a plurality of the aspects of the configuration that have been disclosed. For example, even if some of the aspects of the configuration are eliminated from those illustrated in the embodiments, when the problems described in the "Problems to be Solved" section are solved, and the effects described in the "Effects of the Invention" section are obtained, then the configuration with some aspects eliminated can be extracted as an invention.

According to the present invention, the permeation depth of the evanescent light can always be the same amount regardless of switching the excitation wavelength, and thus the troublesome operation of adjusting of the incident angle for each switching of the excitation wavelength required by the microscopes of the prior art can be omitted, so that the desired fluorescence observation can be easily realized.

Lasers of a plurality of wavelengths can be stably controlled, and by synchronization with the detection system, fluorescence from a multiple dyed specimen can be quickly and selectively obtained. As a result, each of the fluorescence images can be switched and displayed on a monitor (display device), or multiple fluorescence images can be displayed at the same time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A total internal reflection fluorescence microscope comprising:
    a light source which generates laser light having a plurality of wavelengths and which is switchable from generating laser light having one wavelength to generating laser light having another wavelength;
    a focal optical system which irradiates the laser light from the light source on a specimen at a predetermined incident angle via an objective lens and which generates evanescent illumination;
    a fluorescence observation unit which observes fluorescence generated from the specimen due to the evanescent illumination;
    an incident angle adjuster which adjusts the incident angle of the laser light irradiated on the specimen; and
    a controller which controls the incident angle adjuster to maintain an amount of permeation depth of the evanescent light to be the same when the laser light from the laser light source is switched from one wavelength to another.

2. The total internal reflection fluorescence microscope according to claim 1, wherein the controller comprises a storage unit which stores control information on the incident angle which corresponds to the wavelength of the laser from the light source, and controls the incident angle adjuster based on the control information stored in the storage unit in accordance with the switching of the wavelength of the laser light from the laser light source.

3. The total internal reflection fluorescence microscope according to claim 1, wherein the incident angle adjuster comprises a deflection mirror.

4. The total internal reflection fluorescence microscope according to claim 1, further comprising:
    a confocal observation unit which comprises a deflection mirror for deflecting the laser light from the light source, and which scans the specimen with a light spot by deflecting the laser light using the deflection mirror; and
    a focusing optical system which switches between a first state in which the laser light that is deflected by the deflection mirror performs spot illumination on the specimen and a second state in which the specimen is irradiated at a predetermined incident angle via the objective lens and evanescent illumination is generated.

5. The total internal reflection fluorescence microscope according to claim 1, wherein:
    the fluorescence observation unit comprises a fluorescence wavelength selector which selects and transmits the fluorescence generated from the sample for each wavelength, and
    the selection of the fluorescence wavelength by the fluorescence wavelength selector is interlocked with the switching of the wavelength for the laser light.

6. The total internal reflection fluorescence microscope according to claim 5, further comprising a display unit which images the fluorescence for each of the wavelengths detected by the fluorescence observation unit and displays the image as a fluorescence image.

7. The total internal reflection fluorescence microscope according to claim 1, wherein the fluorescence observation unit further comprises a fluorescence detector which detects fluorescence generated from the specimen for each of the wavelengths.

8. The total internal reflection fluorescence microscope according to claim 7, further comprising a display unit which images the fluorescence for each of the wavelengths detected by the fluorescence observation unit and displays the image as a fluorescence image.

9. A total internal reflection fluorescence microscope according to claim 1, further comprising:
    a permeation depth calculator which calculates the depth of permeation of the specimen for total internal reflection illumination from a control value of the incident angle adjuster; and
    a display unit which displays the permeation depth calculated by the permeation depth calculator.

10. A total internal reflection fluorescence microscope according to claim 1, further comprising:
    an input unit which inputs a permeation depth of permeation of the specimen for total internal reflection illumination;

a condition incident angle calculator which calculates conditions for calculating the incident angle to set a depth of permeation of the specimen for total internal reflection illumination to the input permeation depth; and a display unit which displays the conditions obtained by the condition incident angle calculator.

11. A total internal reflection fluorescence microscope comprising:

a light source which generates laser light having a plurality of wavelengths and which is switchable from generating laser light having one wavelength to generating laser light having another wavelength;

a focal optical system which irradiates the laser light from the light source on a specimen at a predetermined incident angle via an objective lens and which generates evanescent illumination;

a fluorescence observation unit which observes fluorescence generated from the specimen due to the evanescent illumination;

an incident angle adjuster which adjusts the incident angle of the laser light irradiated on the specimen; and a controller which controls the incident angle adjuster to set and maintain a permeation depth of the evanescent light at a predetermined amount when the laser light from the laser light source is switched from one wavelength to another;

wherein the controller has a storage unit which stores control information on the incident angle which corresponds to the wavelength of the laser light from the laser light source and controls the incident angle adjuster based on the control information stored in the storage unit in accordance with the switching of the wavelength of the laser light from the laser light source.

12. The total internal reflection fluorescence microscope according to claim 11, wherein the incident angle adjuster comprises a deflection mirror.

13. The total internal reflection fluorescence microscope according to claim 11, further comprising:

a confocal observation unit which comprises a deflection mirror for deflecting the laser light from the light source, and which scans the specimen with a light spot by deflecting the laser light using the deflection mirror; and a focusing optical system which switches between a first state in which the laser light that is deflected by the deflection mirror performs spot illumination on the specimen and a second state in which the specimen is irradiated at a predetermined incident angle via the objective lens and evanescent illumination is generated.

14. The total internal reflection fluorescence microscope according to claim 11, wherein:

the fluorescence observation unit comprises a fluorescence wavelength selector which selects and transmits the fluorescence generated from the sample for each wavelength, and the selection of the fluorescence wavelength by the fluorescence wavelength selector is interlocked with the switching of the wavelength for the laser light.

15. The total internal reflection fluorescence microscope according to claim 14, further comprising a display unit which images the fluorescence for each of the wavelengths detected by the fluorescence observation unit and displays the image as a fluorescence image.

16. The total internal reflection fluorescence microscope according to claim 11, wherein the fluorescence observation unit further comprises a fluorescence detector which detects fluorescence generated from the specimen for each of the wavelengths.

17. The total internal reflection fluorescence microscope according to claim 16, further comprising a display unit which images the fluorescence for each of the wavelengths detected by the fluorescence observation unit and displays the image as a fluorescence image.

18. A total internal reflection fluorescence microscope according to claim 11, further comprising:

a permeation depth calculator which calculates the depth of permeation of the specimen for total internal reflection illumination from a control value of the incident angle adjuster; and a display unit which displays the permeation depth calculated by the permeation depth calculator.

19. A total internal reflection fluorescence microscope according to claim 11, further comprising:

an input unit which inputs a permeation depth of permeation of the specimen for total internal reflection illumination;

a condition incident angle calculator which calculates conditions for calculating the incident angle to set a depth of permeation of the specimen for total internal reflection illumination to the input permeation depth; and a display unit which displays the conditions obtained by the condition incident angle calculator.

20. A total internal reflection fluorescence microscope comprising:

a light source which generates laser light having a plurality of wavelengths;

a varying unit which variably controls the wavelength of the laser light and output intensity;

a focal optical system which irradiates the laser light from the light source on a specimen at a predetermined incident angle via an objective lens and which generates evanescent illumination;

a fluorescence observation unit which comprises a camera and which observes fluorescence generated from the specimen due to the evanescent illumination;

an incident angle adjuster which adjusts the incident angle of the laser light irradiated on the specimen; and a controller, which controls the varying unit and the fluorescence observation unit, and which controls the incident angle adjuster such that an amount of permeation depth of the evanescent light is the same when the wavelength of the laser light from the laser light source is switched from one wavelength to another;

wherein the controller controls the varying unit and synchronizes switching of the wavelengths of the laser light in a time series to irradiate the laser light on the specimen with acquiring of fluorescence images by the camera; and wherein the camera acquires fluorescence images for each of the wavelengths of the laser light.

21. The total internal reflection fluorescence microscope according to claim 20, wherein the controller comprises a storage unit which stores control information of the incident angle which corresponds to the wavelength of the laser light from the light source, and controls the incident angle adjuster based on the control information stored in the storage unit in accordance with the switching of the wavelength of the laser light.

22. The total internal reflection fluorescence microscope according to claim 20, further comprising:

a confocal observation unit which comprises a deflection mirror for deflecting the laser light from the light source, and which scans the specimen with the light spot by deflecting the laser light using the deflection mirror; and a focusing optical system which switches between a first state in which the laser light that is deflected by the deflection mirror performs spot illumination on the specimen and a second state in which the specimen is irradiated at a predetermined incident angle via the objective lens and evanescent illumination is generated.

23. The total internal reflection fluorescence microscope according to claim 20, wherein:

the fluorescence observation unit comprises a fluorescence wavelength selector which selects and transmits the fluorescence generated from the specimen for each wavelength, and the selection of the fluorescence wavelength by the fluorescence wavelength selector follows the switching of the wavelength for the laser light.

24. A total internal reflection fluorescence microscope comprising:

a light source which generates laser light having a plurality of wavelengths;

a varying unit which variably controls the wavelength of the laser light and output intensity;

a focal optical system which irradiates the laser light from the light source on a specimen at a predetermined incident angle via an objective lens and which generates evanescent illumination;

a fluorescence observation unit which comprises a camera and which observes fluorescence generated from the specimen due to the evanescent illumination;

an incident angle adjuster which adjusts the incident angle of the laser light irradiated on the specimen; and a controller, which controls the varying unit and the fluorescence observation unit, and which controls the incident angle adjuster such that a permeation depth of the evanescent light is set to a predetermined amount when the wavelength of the laser light from the laser light source is switched from one wavelength to another;

wherein the controller controls the varying unit and synchronizes switching of the wavelengths of the laser light in a time series to irradiate the laser light on the specimen with acquiring of fluorescence images by the camera; and wherein the camera acquires fluorescence images for each of the wavelengths of the laser light.

25. The total internal reflection fluorescence microscope according to claim 24, wherein the controller comprises a storage unit which stores control information of the incident angle which corresponds to the wavelength of the laser light from the light source, and controls the incident angle adjuster based on the control information stored in the storage unit in accordance with the switching of the wavelength of the laser light.

26. A total internal reflection fluorescence microscope comprising:

a light source;

an incident angle controller which controls an incident angle of illumination light from the light source which is irradiated on a specimen;

a permeation depth calculator which calculates a depth of permeation of the specimen for total internal reflection illumination from a control value of the incident angle controller; and a display unit which displays the permeation depth calculated by the permeation depth calculator;

wherein the light source outputs a plurality of wavelengths, and the total internal reflection fluorescence microscope further comprises:

an incident angle calculator which calculates the incident angle for each wavelength for fixing the permeation depth of total internal reflection illumination for all the wavelengths when the incident angle for one wavelength is selected from the plurality of wavelengths of light output from the light source; and an incident angle display unit which displays the incident angle obtained by the incident angle calculator for each wavelength, and wherein the incident angle controller controls the incident angle in accordance with the irradiated wavelength.

27. A total internal reflection fluorescence microscope comprising:

a light source;

an incident angle controller which controls an incident angle of illumination light from the light source which is irradiated on a specimen;

an input unit which inputs a permeation depth of permeation of the specimen for total internal reflection illumination;

a condition incident angle calculator which calculates conditions for calculating the incident angle to set a depth of permeation of the specimen for total internal reflection illumination to the input permeation depth; and a display unit which displays the conditions obtained by the condition incident angle calculator;

wherein the light source outputs a plurality of wavelengths, and the total internal reflection fluorescence microscope further comprises:

an incident angle calculator which calculates the incident angle corresponding to the inputted permeation depth for at least two wavelengths; and a display unit which displays the incident angle obtained by the incident angle calculator for each wavelength, and wherein the incident angle controller controls the incident angle in accordance with the irradiated wavelength.

* * * * *